United States Patent
Albanna et al.

(10) Patent No.: US 12,415,848 B1
(45) Date of Patent: *Sep. 16, 2025

(54) BONE GELATIN PROCESS

(71) Applicant: Humabiologics, Inc., Phoenix, AZ (US)

(72) Inventors: Mohammad Z. Albanna, Chandler, AZ (US); Nilabh S. Kajave, Tempe, AZ (US)

(73) Assignee: Humabiologics, Inc., Phoenix, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/901,009

(22) Filed: Sep. 30, 2024

Related U.S. Application Data

(63) Continuation-in-part of application No. 18/614,665, filed on Mar. 23, 2024, now Pat. No. 12,104,088.

(60) Provisional application No. 63/454,264, filed on Mar. 23, 2023.

(51) Int. Cl.
  *C07K 14/78* (2006.01)
  *C07K 1/14* (2006.01)

(52) U.S. Cl.
  CPC .............. *C07K 14/78* (2013.01); *C07K 1/145* (2013.01)

(58) Field of Classification Search
  None
  See application file for complete search history.

(56) References Cited

PUBLICATIONS

Mokrej, P., et al. 2019 Polymers 11:1060, 14 pages. (Year: 2019).*
Nichol, J.W., et al. 2010 Biomaterials 31: 5536-5544. (Year: 2010).*
Irmak, G., et al. 2019 ACS Biomater Sci Eng 5: 831-845. (Year: 2019).*
Samatra, M.Y., et al. 2022 Compr Rev Food Sci Food Saf 21: 3153-3176. (Year: 2022).*

* cited by examiner

*Primary Examiner* — Marsha Tsay
(74) *Attorney, Agent, or Firm* — Invention To Patent Services; Alex Hobson

(57) ABSTRACT

A process for the production of bone gelatin includes demineralization of bone using a demineralization solution of acid, wherein the bone is washed for a demineralized time in the demineralization solution to remove soft tissue. The demineralized bone is then pulverized to produce particles of the demineralized bone in a homogenized bone tissue. Lipids are then removed from the homogenized bone tissue using a lipid removal series of washing steps which may include washing the homogenized bone tissue in a series of solutions, including a lipid removal solution and an ethanol solution. Gelatin is then removed from the lipid removed bone tissue in a gelatin extraction process, wherein lipid removed bone tissue is placed in a pepsin solution followed by an extraction solution. The gelatin from the gelatin extracted bone tissue may then be separated and the bone gelatin may then be lyophilized.

17 Claims, 1 Drawing Sheet

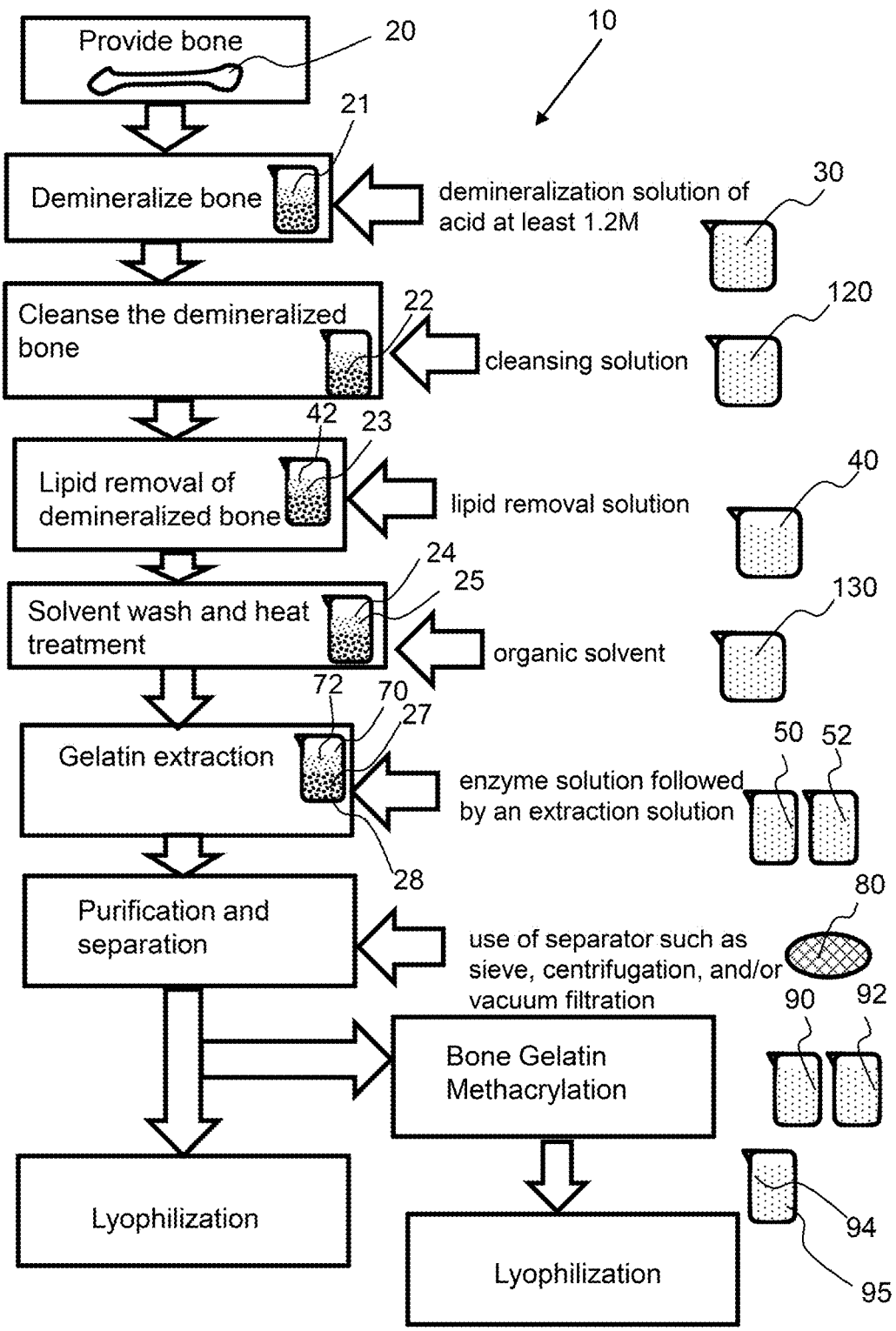

BONE GELATIN PROCESS

CROSS REFERENCE TO RELATED APPLICATIONS

This application is a continuation in part of U.S. patent application Ser. No. 18/614,665, filed on Mar. 23, 2024 and currently pending, which claims the benefit of priority to U.S. provisional patent application No. 63/454,264, filed on Mar. 23, 2023; the entirety of which is hereby incorporated by reference herein.

BACKGROUND OF THE INVENTION

Field of the Invention

The invention relates to a process for the production of bone gelatin.

SUMMARY OF THE INVENTION

The invention is directed to a process for the production of gelatin from bone, or bone gelatin as used to herein. Gelatin is extracted from the collagen in the bone. Gelatin is an irreversibly hydrolyzed form of collagen, wherein the hydrolysis reduces protein fibrils into smaller peptides. An exemplary process includes demineralization of bone using a demineralization solution of acid, such as hydrochloric acid (HCl) or formic acid, wherein the bone is washed for a demineralized time in the demineralization solution to remove bone minerals and soft tissue. The demineralized bone is then pulverized to produce particles of the demineralized bone in a homogenized bone tissue. In an exemplary embodiment, the demineralized bone is homogenized. Lipids are then removed from the homogenized bone tissue using a lipid removal series of washing steps. The lipid removal process may include washing the homogenized bone tissue in a series of solutions, including a lipid removal solution and an organic solvent solution such as ethanol solution. Gelatin is then removed from the lipid removed bone tissue in a gelatin extraction process, wherein lipid removed bone tissue is placed in an enzymatic solution containing an enzyme such as pepsin solution followed by extraction solution, that may be heated, for an extraction time. The gelatin from the gelatin extracted bone tissue may then be separated using a filter, such as a sieve. The bone gelatin may then be lyophilized.

In an exemplary embodiment, before lyophilization, the bone gelatin is subject to gelatin methacrylation, wherein the bone gelatin is combined with a methacrylic anhydride to produce a bone gelatin methacrylic anhydride solution. The bone gelatin methacrylic anhydride solution may be further mixed with a base solution having a pH greater than about 8.0, such as sodium hydroxide solution in a specific pH range to produce bone methacrylate gelatin. The bone gelatin may then be lyophilized. Lyophilization is the process of isolating a solid substance from solution by freezing the solution and vaporizing the ice away under vacuum conditions.

An exemplary demineralization solution is an acid solution such as hydrochloric acid, from 0.1M or more, including but not limited to, about 0.25M or more, about 1M or more, about 1.2M or more, about 2M solution, about 2.5M solution and any range between and including the molar concentrations provided. The bone may be washed in the demineralization solution for a demineralization time of about 1 hour or more, about 5 hours or more, about 8 hours or more, about 10 hours or more about 12 hours or more and any range between and including the demineralization times provided. This demineralization step removes soft tissue coupled with the bone.

An exemplary pulverizing process includes homogenizing the demineralized bone until the bone tissue has an average bone particle of size of no more than 8 mm, no more than 6 mm, no more than 5 mm, no more than 4 mm, no more than 1 mm, or from about 0.5 mm to about 5 mm and any other range between and including the bone particle sizes provided.

An exemplary lipid removal process includes washing the homogenized bone tissue in a series of solutions, including a lipid removal solution and an organic solvent solution, such as an ethanol or other alcohol solution. A lipid removal solution may include chloroform, methanol and/or hexane surfactants, chelants and/or buffers, and/or other organic solvents including but not limited to aliphatic solvents, aromatic solvents, carbonyls solvents. Other lipid removal solution or facilitator may be used in the lipid removal process including, but not limited to, a buffer solution used to maintain pH such as Phosphate Buffered Saline (PBS) or Tri Base, a surfactant, such as Triton, Ethylenediaminetetraacetic Acid (EDTA).

The homogenized bone tissue may be washed in the lipid removal solution for a wash time of about 8 hours or more, about 10 hours or more about 20 hours or more, about 25 hours or more, about 30 hours or more and any range between and including the wash times.

An exemplary ethanol solution includes ethanol with at least water, wherein the ethanol has a concentration of about 50% or more, about 60% or more, about 70% or more, about 80% or more and any range between and including the values provided, such as from about 60% to 70%, for example.

The homogenized bone tissue may be washed in the ethanol solution for a wash time of about 1 hour or more, about 2 hours or more about 3 hours or more, about 4 hours or more, about 5 hours or from about 2 to 4 hours and any range between and including the wash times provided.

The ethanol solution may be heated during the washing of the homogenized bone tissue in the ethanol solution. The ethanol solution may be heated to about 40° C. or more, about 50° C. or more, about 60° C. or more, about 70° C. or more, about 80° C. or less and any range between and including the temperature values provided.

An exemplary pepsin solution may include an acid solution, such as a hydrochloric acid solution combined with pepsin. This process may produce a lipid-free bone tissue. The acid solution may have a molar concentration of about 0.1M or more, about 0.5M or more, about 1.0M solution or more, about 1.2M solution or more about 2M solution, about 2.5M solution and any range between and including the molar concentrations provided. The pepsin may include the pepsin solution in a concentration of about 0.25 mg/ml or more, about 0.5 mg/ml or more about 0.75 mg/ml or more and 1.5M solution or more, about 2M solution, about 2.5M solution and any range between and including the concentrations provided.

In a gelatin extraction process, bone tissue is removed from the pepsin solution and placed in an extraction solution, that may be heated, for an extraction time. The gelatin extraction solution may be heated to about 40° C. or more, about 50° C. or more, about 60° C. or more, about 70° C. or more, about 80° C. or less and any range between and including the temperature values provided.

The homogenized bone tissue may be heated in the gelatin extraction solution for an extraction time of about 1 hour or more, about 2 hours or more about 3 hours or more, about 4 hours or more, about 5 hours or from about 2 to 4 hours and any range between and including the extraction times provided. The gelatin from the gelatin extracted bone tissue may then be separated using a sieve, centrifugation, or vacuum filtration. A sieve or other filter may have an opening size of no more than 5 μm, no more than 3 μm, no more than 1 μm, and any range between and including the opening sizes provided.

The bone gelatin may further be lyophilized, including freezing the bone gelatin and then heating the frozen bone gelatin to a lyophilization temperature of at least 50° C. (70° F.) and drawing vacuum on the bone gelatin; wherein a vacuum pressure is at least 100 mTorr.

The gelatin may be non-dialyzed gelatin, or may be dialyzed to change molecular weight, remove impurities and/or adjust the pH.

Gelatin has several advantages such as good biocompatibility, solubility, and degradability. However, the thermostability of the gelatin is poor which means the gelatin will become a solution above 30° C. due to cleavage of hydrogen bonds. Therefore, combining gelatin with methacrylic anhydride will improve the stability of the gel without affecting the biocompatibility and degradation property of gelatin. The stiffness and porosity of the methacrylated gelatin can be controlled by tuning the hydrogel concentration, degree of functionalization, and UV intensity wherein the bone gelatin is combined with a methacrylic anhydride to produce a bone gelatin methacrylic anhydride solution. The bone gelatin methacrylic anhydride solution may be further be mixed with a base solution such as sodium hydroxide solution in a specific pH range to produce bone methacrylate gelatin. The pH range may be greater than 7.0 but less than 8.0, or less than about 7.5. The bone gelatin methacrylic anhydride solution mixed with a sodium hydroxide solution may be centrifuged to produce the bone methacrylate gelatin.

The methacrylated gelatin may be dialyzed to change molecular weight, remove impurities such as unreacted methacrylic anhydride and/or adjust the pH.

Methacrylated bone gelatin yields higher degree of methacrylation and methacrylolyation indicated by the presence of three peaks from H NMR data compared to non-methacrylated and animal skin gelatin.

The methacrylated bone gelatin may have a degree of methacrylation of about 10% or more, 20% or more, 30% or more, 40% or more, 50% or more, 60% or more, 70% or more, 80% or more, 90% or more, and any range between and including the degree of methacrylation values provided.

The methacrylated bone gelatin may result in a significant reduction of lysine peak compared to the non-methacrylated gelatin.

The methacrylated bone gelatin may have reduction in the lysine group of about 10% or more, 20% or more, 30% or more, 40% or more, 50% or more, 60% or more, 70% or more, 80% or more, 90% or more, and any range between and including the reduction of lysine group values provided.

Methacrylated bone gelatin significantly improved the storage modulus in less time compared to animal skin gelatin.

Methacrylated bone gelatin yields more stable hydrogels as compared to animal skin gelatin.

Methacrylated bone gelatin displayed higher cell viability and improved osteogenic and chondrogenic differentiation of stem cells.

Methacrylated bone gelatin can be used with different types of 3D bioprinters such as extrusion, inkjet, and DLP.

Methacrylated bone gelatin improves the print fidelity of 3D bioprinted constructs.

The bone used in the process described herein may be derived from humans, and more generally mammals such as cows, monkeys, pigs, rats and the like.

A process for the production of bone gelatin may produce a bone gelatin that has a bloom strength selected from low bloom, medium bloom, or high bloom, wherein a low bloom strength has a bloom strength of about 50 to 150 grams, a medium bloom strength has a bloom strength of about 150 to 225 grams and a high bloom strength has a bloom strength of about 225 to 350 grams.

The process for the production of bone gelatin as described herein may utilize endotoxin free or low endotoxin vessels and reagents to produce a low endotoxin bone gelatin having an endotoxin level of about 100 EU/ml or less, about 50 EU/ml or less, about 10 EU/ml or less, or about 1 EU/ml or less and any range between and including the values provided.

The process for the production of bone gelatin may further comprise methacrylation of said bone gelatin. This process may generally include providing a methacrylic anhydride solution and combining the methacrylic anhydride solution with the bone gelatin to produce a methacrylate solution including a methacrylated bone gelatin and residuals.

The methacrylation process may include the following steps:
a. providing a methacrylic anhydride solution:
b. combining the bone gelatin with the buffer (such as Phosphate Buffered Saline (PBS)) to produce a bone gelatin solution;
c. adding the methacrylic anhydride solution to the bone gelatin solution to produce a non-pH adjusted bone gelatin methacrylic anhydride solution;
d. providing a base (such as NaOH) and adding a said base to the bone gelatin methacrylic anhydride solution from step (c) to adjust the pH of the solution to between 7.0 and 8.0, producing a pH adjusted bone gelatin methacrylic anhydride solution;
e. heating and agitating the pH adjusted bone gelatin methacrylic anhydride solution, heated to at least 70° C. for a methacrylation time of at least 2 hours;
f. centrifuging the pH-adjusted bone gelatin methacrylic anhydride solution from step (e) to collect supernatant containing bone methacrylate gelatin; and
g. dialyzing the supernatant containing bone gelatin methacrylic anhydride solution from step (f) against $H_2O$ with the temperature of $H_2O$ between 20-80° C. for at least 1 day to produce methacrylated bone gelatin.

The supernatant may contain the bone methacrylate gelatin and residuals, water and other compounds introduced in the methacrylation process including bases and methacrylic anhydride solution.

The process for the production of bone gelatin may further include, dialyzing the methacrylate solution comprising providing a dialysis separator with a molecular weight cutoff (MWCO) ranging from 1 kDa to 100 kDa and dialyzing the residuals through said dialysis separator. A dialysis separator may be an apparatus, such as a bag or vessel, or other process with a means to separate the residual from the methacrylate solution, such as salt solutions.

The methacrylated bone gelatin produced by the process described herein may have a degree of methacrylation between 80%-100%, such as about 80% or more, about 90% or more and up to about 100%.

The methacrylated bone gelatin may further undergo lyophilization that includes freezing the methacrylated bone gelatin to produce a frozen methacrylated bone gelatin. Subsequently, the frozen methacrylated bone gelatin may be heated a lyophilization temperature of at least 10° C. (50° F.) and vacuum may be drawn on the frozen methacrylated bone gelatin, wherein a vacuum pressure is at least 100 mTorr. This lyophilization may remove liquid from the methacrylated bone gelatin, such as water to produce a lyophilization bone gelatin with a liquid or water concentration of no more than about 10% or less, and preferably about 5% or less, and more preferably 2% or less.

The methacrylated bone gelatin may be sterilized to 6 log reduction level using filtration, ethylene oxide or gamma radiation process. This 6 log reduction means that one in one million chance of an organism surviving in the methacrylated bone gelatin.

The summary of the invention is provided as a general introduction to some of the embodiments of the invention and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

The FIGURE shows a flow diagram of an exemplary process for the production of gelatin from bone.

Corresponding reference characters indicate corresponding parts throughout the several views of the figures. The figures represent an illustration of some of the embodiments of the present invention and are not to be construed as limiting the scope of the invention in any manner. Some of the figures may not show all of the features and components of the invention for ease of illustration, but it is to be understood that where possible, features and components from one figure may be included in the other figures. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for the purpose of illustrating the present invention and should not be interpreted as limiting the scope of the invention. Other embodiments of the invention, and certain modifications, combinations, and improvements of the described embodiments, will occur to those skilled in the art and all such alternate embodiments, combinations, modifications, improvements are within the scope of the present invention.

The FIGURE shows a process for the production of bone gelatin 10 from bone 20. The demineralized bone is treated with a hydrochloric acid solution to demineralize the bone. The lipids are then removed from the bone using a series of solutions. The gelatin is then extracted and subsequently purified. An optional step is bone gelatin methacrylation, as described herein.

As shown in the FIGURE, bone 20 is provided and is demineralized in to demineralized bone 21 using a demineralization solution 30. The demineralization solution may be an acidic solution of at least 1.2M. Then the demineralized bone 21 may be homogenized using a cleansing solution 120 to produce a homogenized bone tissue 22. Then a lipid removal solution 40 is used for lipid 42 removal from the demineralized and homogenized bone tissue. The demineralized bone or homogenized bone tissue is combined with the lipid removal solution 40 for a washing time of at least 8 hours to produce lipid removed bone tissue 23. The lipid removal solution may include chloroform, methanol and hexane.

Then the lipid removed bone tissue 23 may be washed in an organic solvent 130 for an organic solvent wash time to produce a lipid removed washed bone tissue 24. Optionally the lipid removed washed bone tissue 24 is heat by submerging in water that is heated to at least 50° C. to produce a heat-treated washed lipid removed bone tissue 25.

Then in a gelatin extraction step, an enzyme solution 50 followed by an extraction solution 52 is used for gelatin 70 extraction from the lipid removed washed bone tissue 24 to produce processed bone tissue 27 from the gelatin solution 72 to produce said bone gelatin 28. The extraction solution may include water and may be heated to a temperature of at least 40° C.

A separator 80, such as a sieve, filter, centrifuge may be used to separate the processed bone tissue 27 from the gelatin solution 72 to produce said bone gelatin 28.

The bone gelatin 28 may then be subject to methacrylation comprising, providing a methacrylic anhydride solution 90 and combining the bone gelatin with a Phosphate Buffered Saline (PBS) 92 to produce a bone gelatin solution. A buffer or buffer solution may include buffered saline such as a Phosphate Buffered Saline (PBS) or bicarbonate buffer solution. A buffer solution may be a water based salt solution and may be an isotonic buffer solution. The buffer solution may have an osmolarity and ion concentration to match those of the human body. Then the methacrylic anhydride solution 90 may be added to the bone gelatin solution to produce a bone gelatin methacrylic anhydride solution 94. A base solution may include sodium hydroxide (NaOH), lithium hydroxide (LiOH), potassium (KOH) and other strong bases that fully ionize in solution. A base solution may be added to the bone gelatin methacrylic anhydride solution to adjust the pH of the bone gelatin methacrylic anhydride solution to between 7.0 and 7.4. The bone gelatin methacrylic anhydride solution may be heated and agitated for a methacrylation time of at least 2 hours (3-4) to produce a bone methacrylate gelatin solution 95. Bone methacrylate gelatin 29 may be extracted from bone methacrylate gelatin solution 95 using a separator.

The methacrylation process may be optimized for maximizing methacrylation of the bone gelatin to efficiently produce methacrylated bone gelatin. The methacrylation process may be tailored to produce methacrylated bone gelatin with specific levels or combinations of mechanical properties, including stiffness, elasticity, and degradation rate, by varying the degree of methacrylation.

It will be apparent to those skilled in the art that various modifications, combinations, and variations can be made in the present invention without departing from the scope of the invention. Specific embodiments, features and elements described herein may be modified, and/or combined in any suitable manner. Thus, it is intended that the present invention covers the modifications, combinations, and variations of this invention provided they come within the scope of the appended claims and their equivalents.

What is claimed is:

1. A process for the production of bone gelatin comprising:
   a) providing bone;
   b) providing a demineralization solution of acid solution, wherein said acid solution is a hydrochloric acid (HCl) or formic acid having a concentration of 0.1M or more;
   c) demineralization of said bone wherein said bone is washed in said demineralization solution for a demineralization time of 1 hour or more; wherein minerals, ions, or salts are removed from said bone to produce a demineralized bone;
   d) cleansing of the demineralized bone; wherein the demineralized bone is homogenized to produce a homogenized bone tissue;
   e) lipid removal of the homogenized bone tissue comprising:
      i) providing a lipid removal solution comprising an organic solvent selected from the group consisting of: aliphatic solvents, aromatic solvents, carbonyls solvents, ethanol, methanol, hexane and alcohol solution;
      ii) washing the homogenized bone tissue with said lipid removal solution for a washing time of at least 8 hours to produce lipid removed bone tissue;
      iii) providing an organic solvent solution;
      iv) washing the lipid removed bone tissue in said organic solvent solution for an organic solvent wash time to produce a lipid removed washed bone tissue;
      v) heat treating the lipid removed washed bone tissue by submerging said lipid removed washed bone tissue in water, heated to at least 50° C., to produce a heat-treated washed lipid removed bone tissue;
      vi) providing an enzymatic solution containing pepsin solution and wherein the enzymatic solution is acidic;
      vii) washing the heat-treated washed lipid removed bone tissue in the enzyme solution to produce a processed bone tissue;
   f) gelatin extraction of said processed bone tissue comprising:
      i) providing an extraction solution comprising water;
      ii) extracting the gelatin into the extraction solution;
      iii) heating the extraction solution to an extraction temperature of at least 40° C.;
      iv) combining the processed bone tissue with the extraction solution, heated to said extraction temperature of at least 40° C., for an extraction time of at least 1 hour to produce a gelatin solution; and
   g) separating the processed bone tissue from the gelatin solution to produce said bone gelatin.

2. The process for the production of bone gelatin of claim 1, wherein the process produces a low endotoxin bone gelatin having an endotoxin level of less than 100 EU/ml.

3. The process for the production of bone gelatin of claim 1, wherein the organic solvent includes ethanol in water and wherein the ethanol concentration is at least 70%.

4. The process for the production of bone gelatin of claim 1, wherein the organic solvent wash time is at least 8 hours.

5. The process for the production of bone gelatin of claim 1, wherein the enzyme solution has a pH of 5 or less.

6. The process for the production of bone gelatin of claim 1, wherein separation of bone from the gelatin solution includes passing the bone and gelatin solution through a sieve.

7. The process for the production of bone gelatin of claim 1, wherein separating of the processed bone tissue from the gelatin solution includes centrifugation of said bone and gelatin solution.

8. The process for the production of bone gelatin of claim 1, wherein the acid solution is a hydrochloric acid solution with water.

9. The process for the production of bone gelatin of claim 1, wherein said bone is washed in said demineralization solution for a demineralization time of at least 20 hours.

10. The process for the production of bone gelatin of claim 1, further comprising lyophilizing the bone gelatin comprising freezing the bone gelatin then heating the frozen bone gelatin to a lyophilization temperature of at least 10° C. (50° F.) and drawing vacuum on the bone gelatin, wherein a vacuum pressure is at least 100 mTorr.

11. The process of claim 1, wherein the bone gelatin has a low bloom strength between 50 to 150 grams.

12. The process of claim 1, wherein the bone gelatin has a medium bloom strength between 150 to 225 grams.

13. The process of claim 1, wherein the bone gelatin has a high bloom strength between 225 to 350 grams.

14. The process for the production of bone gelatin of claim 1, further comprising methacrylation of said bone gelatin comprising:
   a) providing a methacrylic anhydride solution; and
   b) combining the methacrylic anhydride solution with the bone gelatin to produce a methacrylate solution including a methacrylated bone gelatin and residuals.

15. The process for the production of bone gelatin of claim 14, dialyzing the methacrylate solution comprising providing a dialysis separator with a molecular weight cutoff (MWCO) ranging from 1 kDa to 100 kDa.

16. The process for the production of bone gelatin of claim 14, wherein methacrylated bone gelatin has a degree of methacrylation between 80%-100%.

17. The process for the production of bone gelatin of claim 14, further comprising lyophilization of the methacrylated bone gelatin comprising freezing the methacrylated bone gelatin to produce a frozen methacrylated bone gelatin; and heating the frozen methacrylated bone gelatin to a lyophilization temperature of at least 10° C. (50° F.) and drawing vacuum on the frozen methacrylated bone gelatin, wherein a vacuum pressure is at least 100 mTorr.

* * * * *